US008294755B2

(12) United States Patent  
Mizuno

(10) Patent No.: US 8,294,755 B2  
(45) Date of Patent: Oct. 23, 2012

(54) LIGHT SOURCE APPARATUS AND ENDOSCOPE APPARATUS

(75) Inventor: Kyosuke Mizuno, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 593 days.

(21) Appl. No.: 12/329,737

(22) Filed: Dec. 8, 2008

(65) Prior Publication Data

US 2009/0147079 A1  Jun. 11, 2009

(30) Foreign Application Priority Data

Dec. 6, 2007  (JP) ................................. 2007-316121

(51) Int. Cl.  
*A61B 1/04* (2006.01)  
*A61B 1/00* (2006.01)

(52) U.S. Cl. ............. 348/68; 348/76; 600/118; 600/178

(58) Field of Classification Search .................. None  
See application file for complete search history.

(56) References Cited

U.S. PATENT DOCUMENTS

| 4,834,071 | A | 5/1989 | Hosoi et al. |
| 5,087,122 | A | 2/1992 | Ostrander et al. |
| 5,277,172 | A | 1/1994 | Sugimoto |
| 5,868,666 | A | * | 2/1999 | Okada et al. ................... 600/118 |
| 6,473,116 | B1 | * | 10/2002 | Takahashi ....................... 348/65 |

FOREIGN PATENT DOCUMENTS

| EP | 1 989 995 A1 | 11/2008 |
| JP | 07-184109 | 7/1995 |
| JP | 2000-253307 | 9/2000 |
| JP | 2001-137186 | 5/2001 |
| JP | 2003-325446 | 11/2003 |

* cited by examiner

*Primary Examiner* — Wen-Tai Lin  
(74) *Attorney, Agent, or Firm* — Scully, Scott, Murphy & Presser, P.C.

(57) ABSTRACT

A light source apparatus capable of controlling a quantity of light in a stable manner and an endoscope apparatus including the light source apparatus are provided. The light source apparatus includes a light source and a light quantity adjusting portion for limiting the light flux from the light source using an aperture blade. The light quantity adjusting portion includes the aperture blade which is driven to rotate in a vertical plane about a pivot and has a center of gravity which is decentered from the pivot, a position detecting portion for detecting a position of the aperture blade, a driving portion, and a light source controlling portion for controlling the driving portion. The light source controlling portion controls the driving portion based on the position of the aperture blade and a rotation direction.

4 Claims, 6 Drawing Sheets

VERTICAL DIRECTION

VERTICAL DIRECTION

VERTICAL DIRECTION

VERTICAL DIRECTION

VERTICAL DIRECTION

VERTICAL DIRECTION

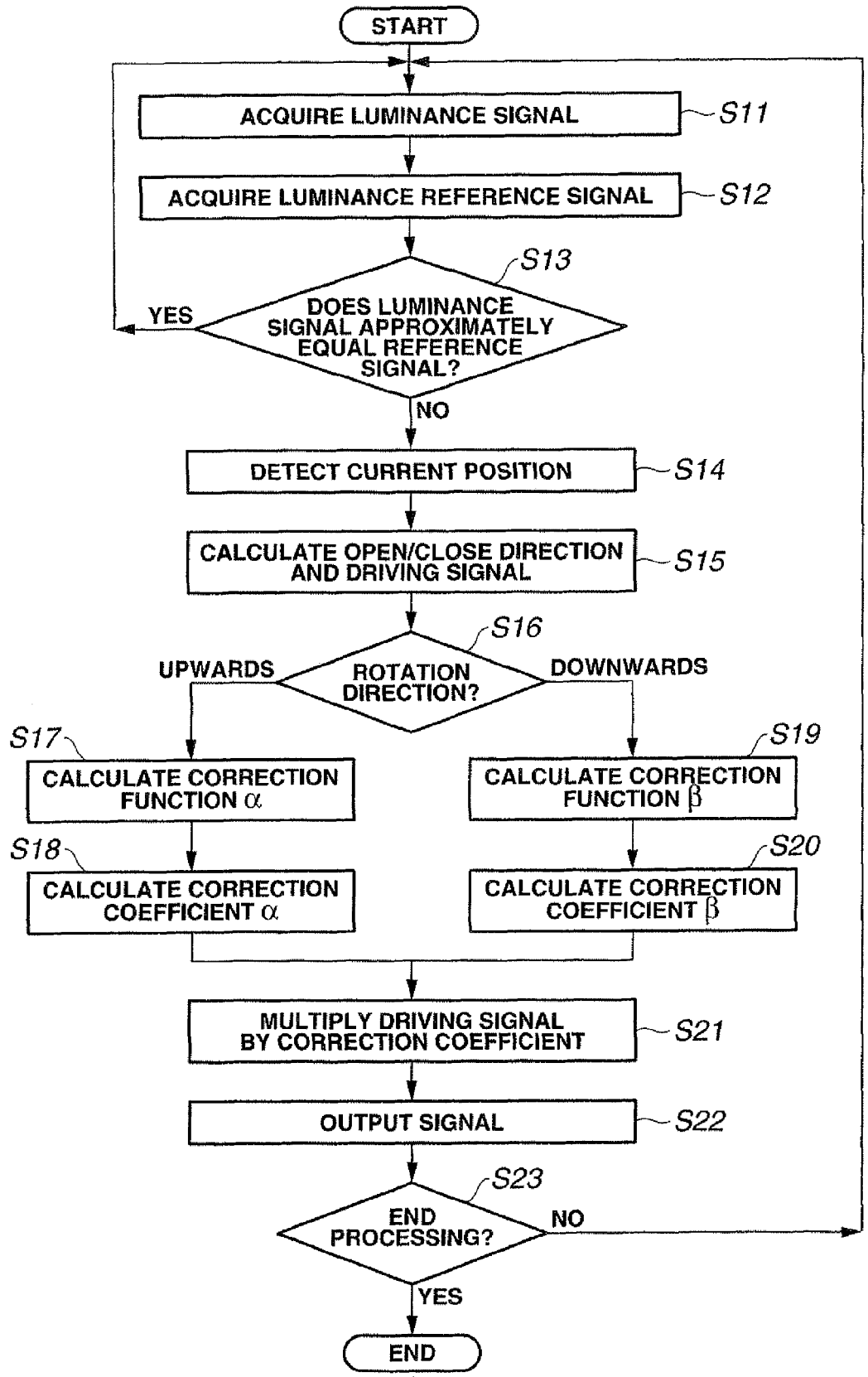

LIGHT SOURCE APPARATUS AND ENDOSCOPE APPARATUS

This application claims benefit of Japanese Application No. 2007-316121 filed in Japan on Dec. 6, 2007, the contents of which are incorporated herein by this reference.

BACKGROUND OF THE INVENTION

1. Field of the Invention

The present invention relates to a light source apparatus equipped with a light quantity adjusting portion for limiting light flux from a light source using an aperture blade and an endoscope apparatus equipped with the light source apparatus.

2. Description of the Related Art

Endoscopes are widely used in the medical field and the like. Endoscopes are constructed to include an elongated insertion portion. Endoscopes allow observation of organs within the body by insertion of the insertion portion into the body. When necessary, various treatments can be performed using treatment instruments introduced through a treatment instrument channel.

Endoscope apparatus including this type of endoscope guides illuminating light from a light source apparatus to illuminate a target site in the test body using a light guide or the like and obtains an endoscopic image by acquiring the return light.

The endoscope apparatus picks up the endoscopic image using an image pickup portion such as a CCD. The endoscopic image is then processed by a signal processing device and displayed on a monitor, allowing an operator to observe the target site.

In the endoscopic apparatus, light from a light source which generates a sufficient quantity of light is collected using an optical system including lenses, and guided through a light guide to the distal end of the insertion portion. Here, a light quantity adjusting portion which limits the light flux with an aperture blade is used to reduce light to a desired quantity of light by limiting light flux from the light source apparatus. For example, Japanese Patent Application Laid-Open Publication No. 2000-253307 discloses the construction shown in FIG. 1 as an aperture blade portion 120 of the light quantity adjusting portion. FIG. 1 is a plan view showing the aperture blade portion 120 seen in a light flux advancing direction. A distal end portion (screen portion) 112a of an aperture blade 112 has a circular form to allow a complete screening of a light flux 110 emitted in parallel from light source. A motor 126 is connected to an end portion side of a plate-like supporting arm 112b extending from the distal end portion 112a, and, when the motor 126 rotates, the aperture blade 112 rotates about a pivot 111 located in the supporting arm 112b. When the aperture blade 112 rotates, the area over which the light flux 110 passes the aperture blade 112, and thus the quantity of light, changes depending on the position of the distal end portion 112a. In the following description, the aperture blade 112 is said to be "closed" when moved into the light flux 110 and "open" when the aperture blade 112 is moved away from the light flux 110.

As shown in FIG. 1, the aperture blade 112 of the aperture blade portion 120 of the light quantity adjusting portion disclosed in Japanese Patent Application Laid-Open Publication No. 2000-253307 rotates in a vertical plane about the pivot 111. However, a center of gravity 130 of the aperture blade 112 is decentered with respect to the pivot 111. In other words, the aperture blade 112 has a form in which the position of the pivot 111 and the center of gravity 130 do not match.

Endoscope apparatus is generally used not only to observe the target site, but also to perform observations while the insertion portion of the endoscope is being inserted. While the insertion portion is inserted, the quantity of return light varies sharply if sites ahead of the CCD are irradiated with the constant quantity of light, making it difficult to recognize the endoscope image displayed on the monitor. Hence, light source apparatus is desired which is capable of maintaining a constant and stable brightness in the endoscope image displayed on the monitor (i.e. a constant luminance).

SUMMARY OF THE INVENTION

To achieve the object, a light source apparatus of the present invention including a light source and a light quantity adjusting portion for limiting light flux from the light source using an aperture blade, the light quantity adjusting portion includes: the aperture blade which is driven to rotate in a vertical plane about a pivot and has a center of gravity which is decentered from the pivot; a position detecting portion for detecting a position of the aperture blade; a driving portion for driving the aperture blade to rotate; and a controlling portion for controlling the driving portion, wherein the controlling portion controls the driving portion based on the position of the aperture blade detected by the position detecting portion and a rotation direction. Further, an endoscope apparatus of the invention includes the light source apparatus.

BRIEF DESCRIPTION OF THE DRAWINGS

FIG. 7 is a flow chart for explaining a flow of processing in the light source controlling portion according to the present embodiment;

DETAILED DESCRIPTION OF THE PREFERRED EMBODIMENTS

The following describes an endoscope apparatus 1 according to an embodiment of the present invention with reference to the drawings.

Figure 1:
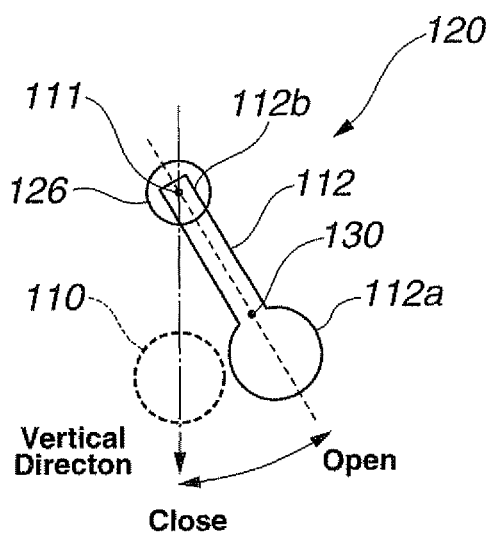
FIG. 1 is a plan view of a conventional aperture blade portion seen in a light flux advancing direction.
Figure 2:
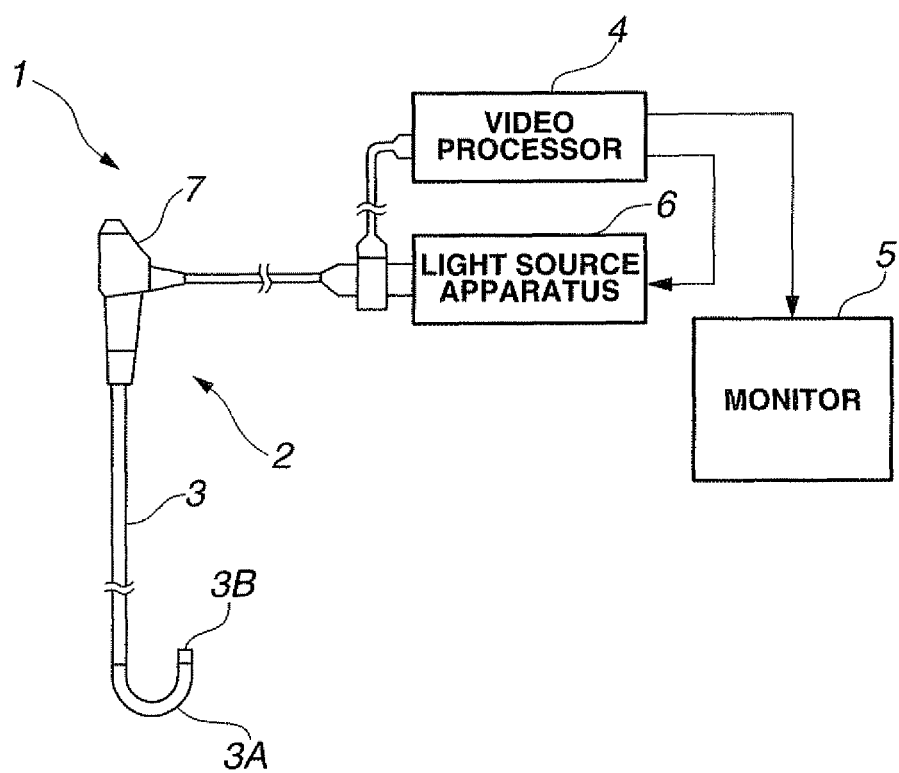
FIG. 2 is a diagram showing an overall configuration of an endoscope apparatus of an embodiment.
Figure 3:
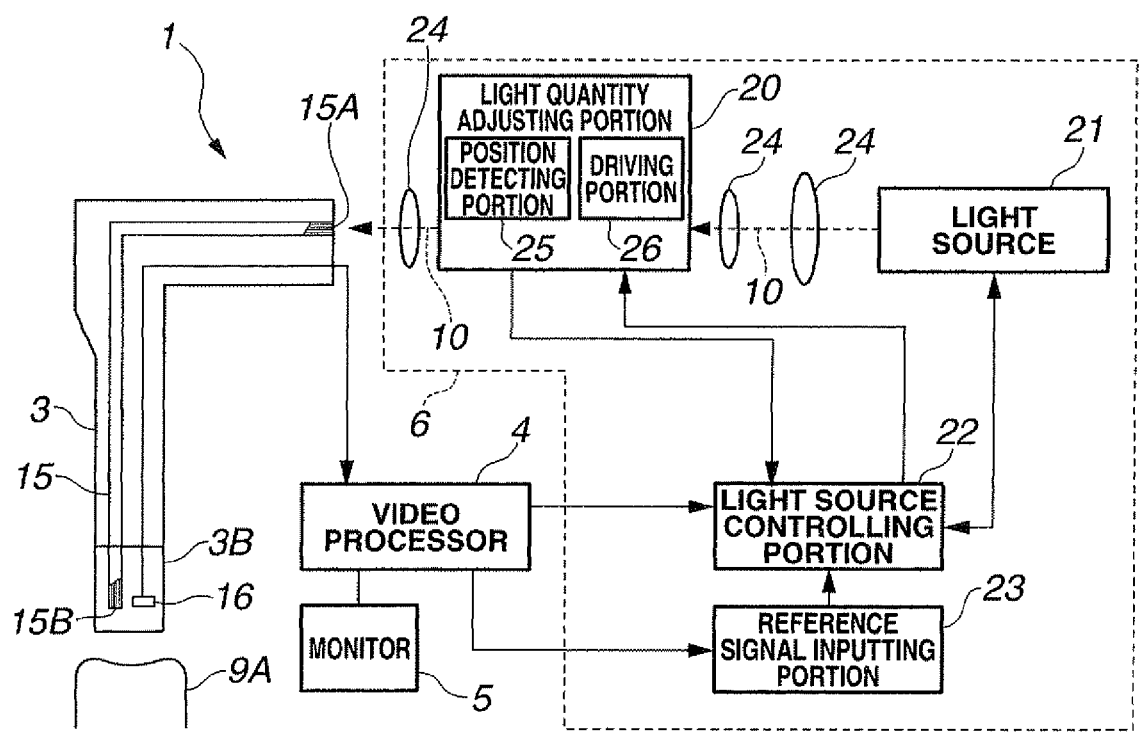
FIG. 3 is a diagram showing a configuration of a light source apparatus of the embodiment.

FIG. 2 is a diagram showing an overall configuration of the endoscope apparatus 1 according to the present embodiment, and FIG. 3 is a diagram showing the configuration of a light source apparatus 6. As shown in FIG. 2, the endoscope apparatus 1 includes an endoscope 2, the light source apparatus 6, a video processor 4, and a monitor 5. The endoscope 2 includes an elongated insertion portion 3 for insertion into the test body, and an operation portion 7 provided at a proximal end of the insertion portion 3. The insertion portion 3 has a bending portion 3A provided at a distal end side of a flexible tube portion which exhibits flexibility, and a distal end portion 3B provided at a distal end side of the bending portion 3A. The distal end portion 3B has a built-in CCD 16 (see FIG. 3) which is an image pickup device for picking up an image of an observation target site 9A within the test body. An image signal from the CCD 16 is processed by the video processor 4 and displayed on a display screen of the monitor 5. Illuminating light supplied from the light source apparatus 6 is delivered to the distal end portion of the insertion portion 3 by a light guide 15 (see FIG. 3) provided within the insertion portion 3.

Thus, as shown in FIG. 3, the light supplied from a light source 21 of the light source apparatus 6 is collected to form light flux 10 by an optical system including lenses 24 and the like, and the light flux 10 is adjusted in quantity by a light quantity adjusting portion 20 and then guided to an end portion 15A of the light guide 15. The illuminating light then passes through the light guide 15 and reaches the other end portion 15B of the light guide 15 provided in the distal end portion 3B. The illuminating light then passes through an illuminating optical system (not shown) provided at an end surface of the end portion 15B, and illuminates the observation target site 9A within the test body.

Here, when the brightness (luminance) of the target image displayed on the monitor 5 varies according to the distance between the observation target site 9A and the distal end portion 3B of the insertion portion 3 or according to the reflectance and the like of the observation target site, the operator may find it difficult to accurately recognize the observation target site 9A. For this reason, a light source controlling portion 22, which is the controlling portion, in the light source apparatus 6 controls a driving portion 26, of the light quantity adjusting portion 20 so that a luminance signal from the video processor 4 is substantially the same as a reference luminance signal inputted from a reference signal inputting portion 23.

Figure 4A:
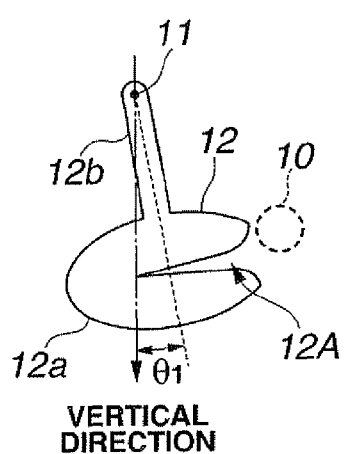
FIG. 4A is a plan view of an aperture blade of a light quantity adjusting portion seen in a light flux advancing direction for explaining the adjustment of a quantity of light using the aperture blade according to the present embodiment, and shows the aperture blade in a fully open state.
Figure 4B:
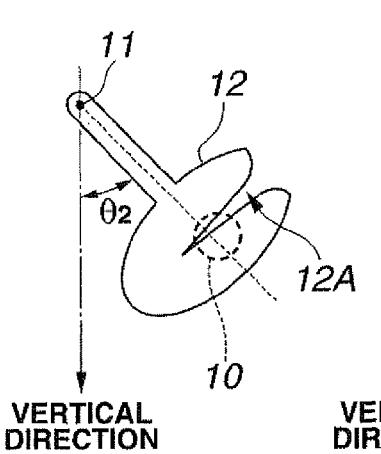
FIG. 4B is a plan view of the aperture blade of the light quantity adjusting portion seen in the light flux advancing direction for explaining the adjustment of a quantity of light using the aperture blade according to the present embodiment, and shows the aperture blade in a partially closed state.
Figure 4C:
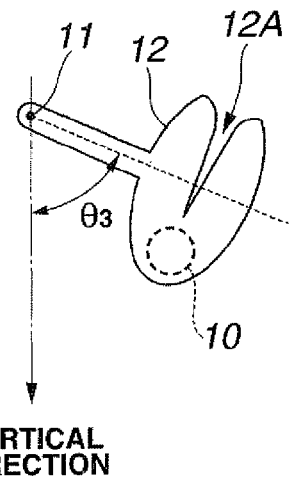
FIG. 4C is a plan view of the aperture blade of the light quantity adjusting portion seen in the light flux advancing direction for explaining the adjustment of a quantity of light using the aperture blade according to the present embodiment, and shows the aperture blade in a fully closed state.

Here, as shown in FIGS. 4A to 4C, the light quantity adjusting portion 20 of the present embodiment limits the light flux 10 from the light source by driving the aperture blade 12 to rotate about a pivot 11 in a vertical plane. FIGS. 4A to 4C are plan views showing the aperture blade 12 seen in the light flux advancing direction for explaining the adjustment of the quantity of light using the aperture blade 12. FIG. 4A shows the aperture blade 12 in a fully open state, FIG. 4B in a partially closed state, and FIG. 4C in a fully closed state.

The aperture blade 12 is made up of a substantially elliptical distal end portion 12a which has a cut-out portion 12A and an elongated plate-form supporting portion 12b extending from the distal end portion. A motor, which is the driving portion 26, and a potentiometer or the like for measuring the rotation angle are connected at the opposite end of the supporting portion 12b to the distal end portion 12a. Note that neither the motor nor the potentiometer is shown in the drawings. The output from the potentiometer is converted to a position of the aperture blade 12, such as a center of gravity angle (described in a later section), by a position detecting portion 25.

When the motor rotates, the aperture blade 12 is driven to rotate about the pivot 11 located in the supporting portion 12b. Then, the quantity of light emitted from the light quantity adjusting portion 20 is adjusted by blocking the light flux 10 with the aperture blade 12 of the light quantity adjusting portion 20. The light quantity adjusting portion 20 which limits the light flux 10 from the light source 21 by driving the aperture blade 12 to rotate has a simple structure and is capable of a fast response.

Note that the aperture blade 12 has the above-described form because of the need to reduce the weight of the aperture blade 12 in order to improve the speed of response. Note also that the center of gravity of the aperture blade 12 of the above form is decentered from the pivot 11 and lies within the distal end portion 12a.

By using the aperture blade 12 in the light quantity adjusting portion 20 with the center of gravity that is decentered with respect to the pivot, the mass of the aperture blade 12 is reduced and responsiveness at high frequencies is realized.

By using a circular aperture blade centered at the pivot, or by attaching a weight on the opposite side of the distal end portion across from the pivot of the supporting portion, the position of center of gravity of the aperture blade could be matched to the position of the pivot. However, since an aperture blade having a center of gravity which lies over the pivot would be heavier and the speed of response decreases, such an aperture blade is not desirable for the light source apparatus of an endoscope apparatus or the like in which it is necessary to adjust the quantity of light quickly.

Figure 5A:
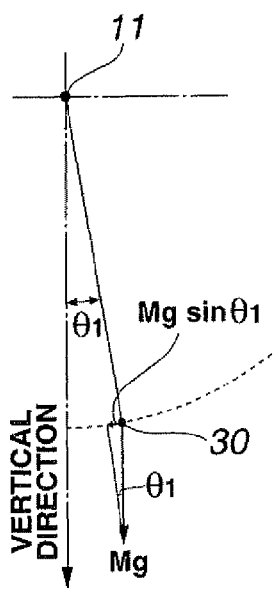
FIG. 5A is a plan view showing the aperture blade of the light quantity adjusting portion seen in the light flux advancing direction for explaining the effects of self-weight with position of the aperture blade according to the present embodiment, and shows the aperture blade in a fully open state.
Figure 5B:
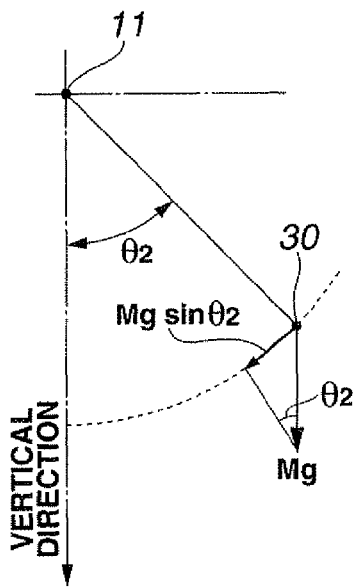
FIG. 5B is a plan view showing the aperture blade of the light quantity adjusting portion seen in the light flux advancing direction for explaining the effects of self-weight with position of the aperture blade according to the present embodiment, and shows the aperture blade in a partially closed state.
Figure 5C:
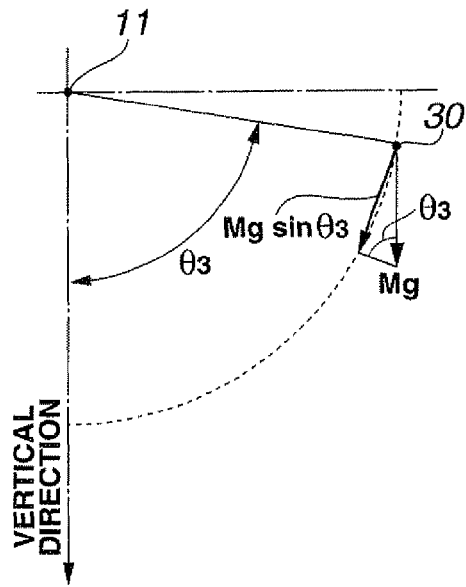
FIG. 5C is a plan view showing the aperture blade of the light quantity adjusting portion seen in the light flux advancing direction for explaining the effects of self-weight with position of the aperture blade according to the present embodiment, and shows the aperture blade in a fully closed state.

The following describes variation in the effects of self-weight with the position of the aperture blade 12 of the light quantity adjusting portion 20 using FIGS. 4A to 4C and FIGS. 5A to 5C. FIGS. 5A to 5C are plan views showing the movement of the center of gravity of the aperture blade 12 seen in the light flux advancing direction for explaining the effects of self-weight with the position of the aperture blade 12. FIG. 5A shows the fully open state, FIG. 5B the partially closed state, and FIG. 5C the fully closed state. Note that, in FIGS. 4A to 4C and FIGS. 5A to 5C, θ1 to θ3 represent the angles (hereinafter referred to as center of gravity angles) formed between a straight line joining the center of gravity 30 of the aperture blade 12 and the pivot 11 and the vertical direction in the respective states.

When the aperture blade 12 is moved in a closing direction (from the state shown in FIG. 4A to that shown in FIG. 4B or from the state shown in FIG. 4B to that shown in FIG. 4C), i.e. rotated in an upwards direction, the rotation must work against gravity. Conversely, when the aperture blade 12 is moved in an opening direction (from the state shown in FIG. 4C to that shown in FIG. 4B or from the state shown in FIG. 4B to that shown in FIG. 4A), i.e. rotated in a downwards direction, the rotation is helped by gravity.

Thus, as shown in FIG. 5, when the center of gravity angle of the aperture blade 12 of mass M is "θ", a rotation direction component "Mg sin θ" of the self-weight of the aperture blade 12 acts in the rotation direction. As the value of the center of gravity angle θ increases, the rotation direction component of the self-weight of the aperture blade 12 also increases. For instance, when the aperture blade 12 is rotated from the state shown in FIG. 5B to the state shown in FIG. 5C, the rotation direction component of the self-weight of the aperture blade 12 increases from "Mg sin θ2" to "Mg sin θ3". Thus, if the light source controlling portion 22 controls the rotation of the aperture blade 12 with an identical output signal, the rotation speed of the aperture blade 12 will drop. Conversely, when the aperture blade 12 is rotated from the state shown in FIG. 5B to the state shown in FIG. 5A, the rotation direction component of the self weight of the aperture blade 12 is decreased from "Mg sin θ2" to "Mg sin θ1". Thus, if the light source controlling portion 22 controls the rotation of the aperture blade 12 with an identical output signal, the rotation speed of the aperture blade 12 will increase. However, the light source controlling portion 22 of the present embodiment controls the rotation of the aperture blade 12 with an output signal which has been corrected using a correction coefficient, and so a stable rotation speed is obtained.

Figure 6A:
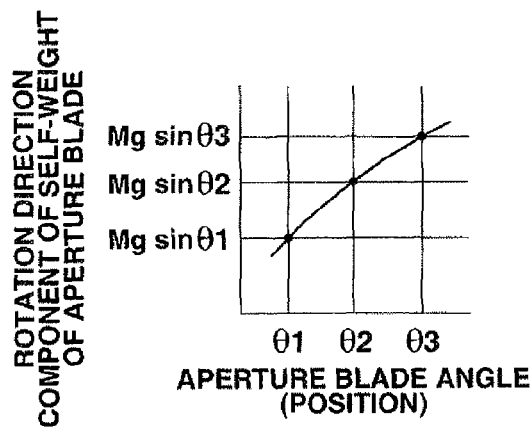
FIG. 6A is a diagram for explaining a correction coefficient used in control performed by a light source controlling portion according to the embodiment.
Figure 6B:
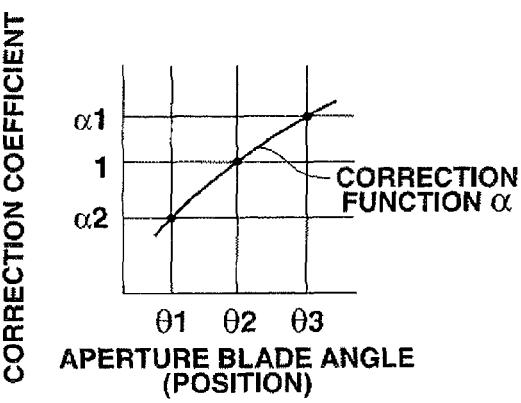
FIG. 6B is a diagram for explaining the correction coefficient used in control performed by the light source controlling portion according to the embodiment.
Figure 6C:
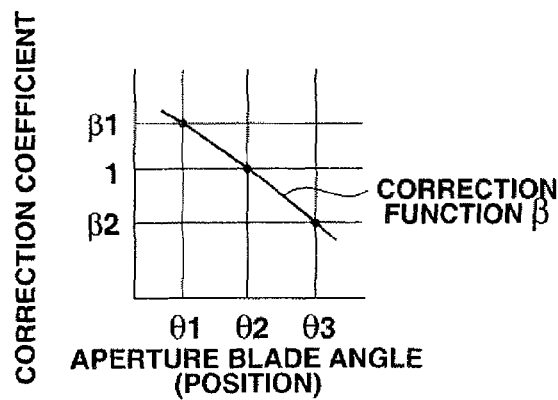
FIG. 6C is a diagram for explaining the correction coefficient used in control performed by the light source controlling portion according to the embodiment.

The following describes the operations of the above-described light source controlling portion 22 in detail with reference to FIGS. 6A to 6C. FIGS. 6A to 6C are diagrams for explaining the correction coefficient for the control performed by the light source controlling portion 22. As shown in FIG. 6A, the rotation direction component of the self-weight of the aperture blade 12 varies with the center of gravity angle θ of the aperture blade 12. To deal with this change, the light source controlling portion 22 of the present embodiment controls the driving portion 26 of the light quantity adjusting portion 20 using an output signal which has been corrected using a correction coefficient calculated based on the position and rotation direction of the aperture blade 12.

Thus, the light source controlling portion 22 may make use of a correction coefficient α from a correction function α when the aperture blade 12 is rotating upwards (i.e. rotating in a closing direction) as shown in FIG. 6B. In FIG. 6B, a correction coefficient α1 for when the aperture blade 12 moves from a current position corresponding to center of gravity angle θ2 to a target position corresponding to center of gravity angle θ3 is given by α1 (Mg sin θ3)/(Mg sin θ2). In other words, α1 is the ratio between the rotation direction component of the self-weight of the aperture blade in the current position and the rotation direction component of the self-weight of the aperture blade in the target position. Note that the rotation direction component of the self-weight of the aperture blade 12 in the position corresponding to the center of gravity angle θ2, which is "Mg sin θ2", is used as a reference and defined as being "1".

The correction coefficient α2 for the movement to a target position corresponding to a center of gravity angle θ1 is calculated in the same way as α1, and the correction function α is calculated by curve fining as shown in FIG. 6B.

When, on the other hand, the aperture blade 12 is rotated downwards (i.e. in an opening direction), a correction coefficient β is calculated from a correction function β as shown in FIG. 6C. In FIG. 6, a correction coefficient β1 for when the aperture blade 12 moves from a current position corresponding to the center of gravity angle θ2 to a target position corresponding to the center of gravity angle θ1 is given by β1=(Mg sin θ2)/(Mg sin θ1). In other words, β1 is the ratio between the rotation direction component of the self-weight of the aperture blade in the current position and the rotation direction component of the self-weight of the aperture blade in the target position. Note that the rotation direction component of the self-weight of the aperture blade 12 in the position corresponding to the center of gravity angle θ2, which is "Mg sin θ2", is used as reference and defined as being "1".

The correction coefficient β2 for the movement to a target position corresponding to the center of gravity angle θ3 is calculated in the same way as β1, and the correction function β is calculated by curve fitting as shown in FIG. 6C.

The light source controlling portion 22 then controls the driving portion 26 with a control signal which has been corrected using the correction coefficient calculated from the correction function using the center of gravity angle θ calculated by the position detecting portion 25. Here, the control signal is a current, voltage or power supplied to the driving portion.

Since the light source controlling portion 22 performs the control using the correction coefficients based on the rotation direction component of the self-weight of the aperture blade 12, the speed of movement is stabilized (i.e. the time taken for the aperture blade 12 to reach the target position from the current position is constant) and independent of the rotation direction or position of the aperture blade 12. It is therefore possible for the light source apparatus 6 to control the quantity of light in a stable manner with a constant response speed.

The following describes a flow of processing of the light source controlling portion 22 with reference to FIG. 7. FIG. 7 is a flowchart for explaining the flow of processing in the light source controlling portion 22.

(Step S11)

First, the light source controlling portion 22 acquires a luminance signal from the video processor 4. The luminance signal is information about an average brightness of the display screen displayed on the monitor 5 for the video signal acquired by the CCD 16 and processed by the video processor 4. Note that information of only a specific part of display screen displayed on the monitor 5 may alternatively be used as the luminance signal.

(Step S12)

The light source controlling portion 22 acquires the reference luminance signal from the reference signal inputting portion 23. The reference luminance signal is a target value for the brightness of the display screen displayed on the monitor 5. The reference luminance signal may be inputted by an operator using a dial or the like provided on the reference signal inputting portion 23. Alternatively, a luminance signal from the video processor 4 at a certain moment may be inputted as the reference luminance signal.

(Step S13)

The light source controlling portion 22 compares the luminance signal and the reference luminance signal and determines whether the difference is within a range of predetermined values. When the difference between the luminance signal and the reference luminance signal is within the range of predetermined values (Yes), the light source controlling portion 22 is not required to drive the aperture blade 12 and the operations from step S11 will be repeated. On the other hand, when the difference between the luminance signal and the reference luminance signal is outside the range of predetermined values, the light source controlling portion 22 performs the operations from step S14 to drive the aperture blade 12.

Note that the predetermined values of the difference between the luminance signal and the reference luminance signal are determined by the operator or when the light source apparatus 6 is designed. If the predetermined values are too small, the aperture blade 12 is constantly driven in small amounts, and the display screen of the monitor 5 may flicker due to the effects of the slow response of the light quantity adjusting portion 20 or the like. Conversely, if the predetermined values are too large, the aperture blade 12 is not driven even when driving is required, and the brightness of the display screen of the monitor 5 is inappropriate.

(Step S14)

The light source controlling portion 22 acquires information about a current position of the aperture blade 12, such as the center of gravity angle $\theta$, from the position detecting portion 25.

(Step S15)

The light source controlling portion 22 calculates a rotation direction and rotation amount (i.e. a driving signal) from the difference between the luminance signal and the reference luminance signal calculated in step S13 and information about the current position of the aperture blade 12 acquired in step S14. Here, the rotational direction is one of the opening direction of the aperture blade 12 (i.e. downwards) and the closing direction of the aperture blade 12 (i.e. upwards). The rotation amount is calculated by finding in advance the relationship between the position (i.e. the angle) of the aperture blade 12 and a quantity of light emitted from the light quantity adjusting portion 20.

(Step S16)

The light source controlling portion 22 determines the correction coefficient for use from the rotation direction of the aperture blade 12 calculated in step S15. The correction coefficient used in the control signal differs according to the rotation direction. Thus, the light source controlling portion 22 performs the processing from step S17 when the rotation direction of the aperture blade 12 is upwards and the processing from step S19 when the rotation direction of the aperture blade 12 is downwards.

(Step S17)

When the aperture blade 12 rotates upwards, the light source controlling portion 22 calculates the correction function $\alpha$ which is a relationship, of the type shown in FIG. 6B, between the center of gravity angle $\theta$ and the correction coefficient $\alpha$. Note that there is no need to calculate the correction function $\alpha$ every time, and a pre-calculated correction function $\alpha$ may be used.

(Step S18)

When the aperture blade 12 rotates upwards, the light source controlling portion 22 calculates the correction coefficient $\alpha$ by substituting the center of gravity angle $\theta$ corresponding to the current position of the aperture blade 12 into the correction function $\alpha$.

(Step S19)

When the aperture blade 12 rotates downwards, the light source controlling portion 22 calculates the correction function $\beta$ which is relationship, of the type shown in FIG. 6C, between the center of gravity angle $\theta$ and the correction coefficient $\beta$. Note that there is no need to calculate the correction function $\beta$ every time, and a pre-calculated correction function $\beta$ may be used.

The correction function $\alpha$ and the correction function $\beta$ are not limited to curve approximation formula of the type shown in FIG. 6B and a straight-line approximation formula or theoretical formula can be used. Another possibility is to use, in place of the functional form, a table form which includes fixed intervals of $\theta$ and corresponding correction coefficients for the correction function $\alpha$ and the correction function $\beta$.

(Step S20)

When the aperture blade 12 rotates downwards, the light source controlling portion 22 calculates the correction coefficient $\beta$ by substituting the center of gravity angle $\theta$ corresponding to the current position of the aperture blade 12 into the correction function $\beta$.

(Step S21)

The light source controlling portion 22 corrects the driving signal calculated in step S15 by finding the product of the driving signal and the correction coefficient $\alpha$ or the correction coefficient $\beta$.

(Step S22)

The light source controlling portion 22 outputs the corrected driving signal to the driving portion 26. The driving portion 26 drives the aperture blade 12 in accordance with the corrected driving signal.

(Step S23)

The light source controlling portion 22 repeats the processing from step S11 until an instruction to end operation is received. As described above, the light quantity adjusting portion 20 of the light source apparatus 6 of the present embodiment includes the light source controlling portion 22 which controls the driving portion 26 using the driving signal which has been corrected based on the position and rotation direction of the aperture blade 12. Hence, it is possible to control the quantity of light in a stable manner and with a fast response. And, the endoscope apparatus 1 including the light source apparatus 6 of the present embodiment, which is capable of controlling the quantity of light in a stable manner and with a fast response, maintains a stable brightness on the monitor screen even when, for instance, observations are made while the insertion portion 3 of the endoscope 2 is being inserted.

Modifications of the Embodiment

The following describes, with reference to the drawings, aperture blades of the light source apparatus which are modifications of the embodiment of the present invention. Since the basic configuration of the light source apparatus of the modifications is substantially the same as that of the light source apparatus 6, the components which are the same are marked with the same reference symbols and descriptions of these components are omitted, and the following description is restricted to the aperture blades.

Note that the aperture blades of the light source apparatus of the present modification, which are described below, are all driven to rotate in vertical plane around a pivot and formed with a center of gravity that is decentered with respect to the pivot in the same way as the aperture blade 12 of the light source apparatus 6 of the embodiment.

Figure 8A:
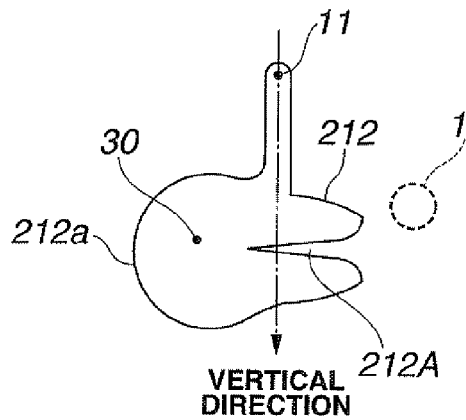
FIG. 8A is a plan view of an aperture blade of the light quantity adjusting portion seen in the light flux advancing direction for explaining a form of the aperture blade according to a modification of the embodiment.
Figure 8B:
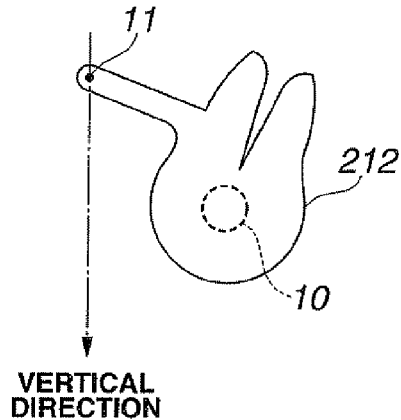
FIG. 8B is a plan view of an aperture blade of the light quantity adjusting portion seen in the light flux advancing direction for explaining a form of the aperture blade according to the modification of the embodiment.

An aperture blade 212 shown in FIG. 8A, for instance, is configured with a particularly large area on the opposite side of the cut-out portion 212a of the distal end portion 212A to prevent leakage of the light flux 10 from around the edge of the distal end portion 212A when the aperture blade 212 blocks the light flux 10 (FIG. 8B). As a result, a center of gravity 30 of the aperture blade 212 is particularly largely decentered with respect to the pivot 11.

Figure 9A:
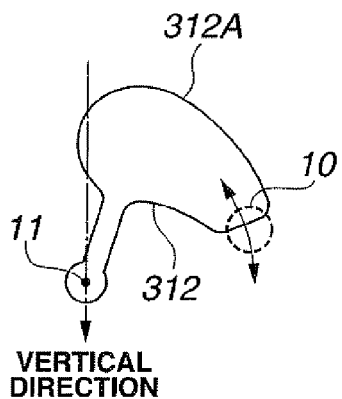
FIG. 9A is a plan view of an aperture blade of the light quantity adjusting portion seen in the light flux advancing direction for explaining a form of the aperture blade according to a modification of the embodiment.

Further, an aperture blade 312 shown in FIG. 9A is configured to block the light flux 10 when the distal end portion 312A rotates downwards. In other words, the rotation directions of the aperture blade and the opening and closing directions for the light flux 10 are the opposite of those for the aperture blade 12 of the light source apparatus 6 of the present embodiment. The aperture blade 312 is driven with a driving signal which has been corrected using correction coefficients which are the reverse of the correction coefficient α and the correction coefficient β of the light source apparatus 6 of the embodiment.

Figure 9C:
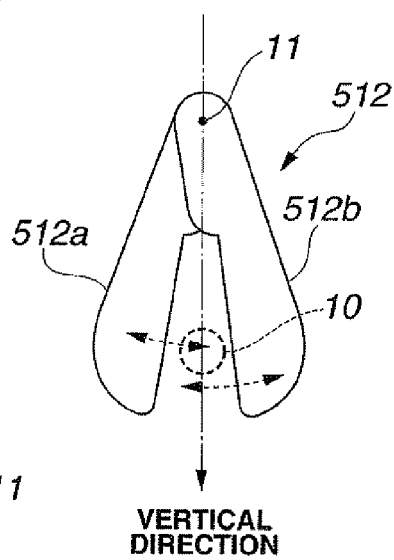
FIG. 9C is a plan view of aperture blades of the light quantity adjusting portion seen in a light flux advancing direction for explaining a form of the aperture blades according to a further modification of the present embodiment.
Figure 9D:
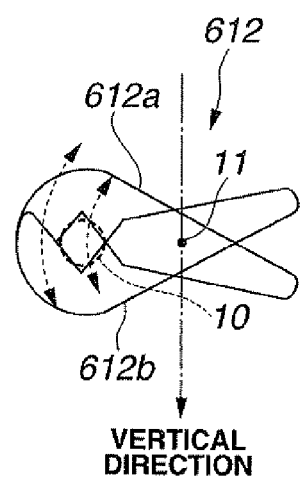
FIG. 9D is a plan view of aperture blades of the light quantity adjusting portion seen in the light flux advancing direction for explaining a form of the aperture blades according to a further modification of the present embodiment.
Figure 9B:
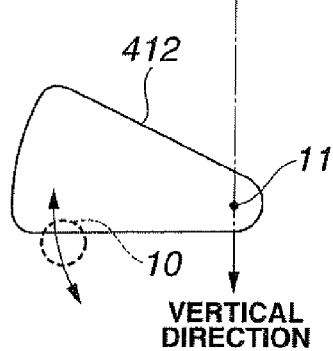
FIG. 9B is a plan view of an aperture blade of the light quantity adjusting portion seen in the light flux advancing direction for explaining a form of the aperture blade according to another modification of the embodiment.

For an aperture blade 412 shown in FIG. 9B, the rotation directions of the aperture blade and the opening and closing directions for the light flux are also the opposites of those for the aperture blade 12 of the light source apparatus 6 of the embodiment. In addition, the distal end portion and the supporting portion have an integrated form.

An aperture blade 512 shown in FIG. 9C limits the light flux 10 through rotation of two aperture blades 512a and 512b in opposite directions. With such an arrangement, the two aperture blades 512a and 512b are each driven with a driving signal corrected using one of the correction coefficient α and the correction coefficient β.

An aperture blade 612 shown in FIG. 9D also limits the light flux 10 through rotation of two aperture blades 612a and 612b in opposite directions.

With a light source apparatus including any of the aperture blades 312 to 612 of the above described modifications, it is possible to obtain the same advantages as those with the light source apparatus 6 of the embodiment of the present invention. Moreover, with an endoscope apparatus equipped with the light source apparatus having any of the aperture blades 312 to 612 of the modifications, it is possible to obtain the same advantages as those with the endoscope apparatus 1 which includes the light source apparatus 6 of the embodiment of the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A light source apparatus including a light source and a light quantity adjusting portion for limiting light flux from the light source using an aperture blade, the light quantity adjusting portion comprising:
    the aperture blade configured to be driven to rotate in a vertical plane about a pivot and has a center of gravity, the center of gravity being decentered from the pivot;
    a position detecting portion for detecting a position of the aperture blade;
    a driving portion for driving the aperture blade to rotate; and
    a controlling portion for controlling the driving portion, wherein
    the controlling portion controls the driving portion based on the position of the aperture blade detected by the position detecting portion and a rotation direction
    wherein the controlling portion is configured to perform the control such that a speed of movement is constant independently of the rotation direction and the position of the aperture blade, using a correction coefficient based on a rotation direction component of self-weight of the aperture blade.

2. The light source apparatus of claim 1, wherein
    the correction coefficient is a ratio of a rotation direction component of self-weight of the aperture blade in a current position and the rotation direction component of self-weight of the aperture blade in a target position.

3. An endoscope apparatus having a light source and a light quantity adjusting portion for limiting light flux from the light source using an aperture blade, the light quantity adjusting portion comprising:
    the aperture blade configured to be driven to rotate in a vertical plane about a pivot and has a center of gravity, the center of gravity being decentered from the pivot;
    a position detecting portion for detecting a position of the aperture blade;
    a driving portion for driving the aperture blade to rotate; and
    a controlling portion for controlling the driving portion, wherein
    the controlling portion controls the driving portion based on the position of the aperture blade detected by the position detecting portion and a rotation direction
    wherein the controlling portion is configured to perform the control such that a speed of movement is constant independently of the rotation direction and the position of the aperture blade, using a correction coefficient based on a rotation direction component of self-weight of the aperture blade.

4. The endoscope apparatus of claim 3, wherein
    the correction coefficient is a ratio of a rotation direction component of self-weight of the aperture blade in a current position and the rotation direction component of self-weight of the aperture blade in a target position.

* * * * *